United States Patent
Gao et al.

(10) Patent No.: US 11,214,788 B2
(45) Date of Patent: Jan. 4, 2022

(54) TRIPTERYGIUM WILFORDII CRYPTOMERIDIOL SYNTHASE, CODING GENE THEREOF AND RECOMBINANT YEAST CONTAINING CODING GENE

(71) Applicant: CAPITAL MEDICAL UNIVERSITY, Beijing (CN)

(72) Inventors: Wei Gao, Beijing (CN); Luqi Huang, Beijing (CN); Yuru Tong, Beijing (CN); Tianyuan Hu, Beijing (CN)

(73) Assignee: CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 16/968,338

(22) PCT Filed: Jan. 30, 2019

(86) PCT No.: PCT/CN2019/073905
§ 371 (c)(1),
(2) Date: Aug. 7, 2020

(87) PCT Pub. No.: WO2019/154217
PCT Pub. Date: Aug. 15, 2019

(65) Prior Publication Data
US 2021/0171930 A1   Jun. 10, 2021

(30) Foreign Application Priority Data
Feb. 9, 2018   (CN) .......................... 201810133374.9

(51) Int. Cl.
C12N 9/88 (2006.01)
C12N 9/04 (2006.01)
C12N 15/81 (2006.01)

(52) U.S. Cl.
CPC .............. *C12N 9/88* (2013.01); *C12N 9/0006* (2013.01); *C12N 15/81* (2013.01); *C12Y 101/01034* (2013.01)

(58) Field of Classification Search
CPC .................................. C12N 9/88; C12N 15/81
USPC ....................................................... 435/232
See application file for complete search history.

(56) References Cited

FOREIGN PATENT DOCUMENTS

CN   108330122 A   7/2018
CN   108359615 A   8/2018

OTHER PUBLICATIONS

Donald et al., "Effects of Overproduction of the Catalytic Domain of 3-Hydroxy-3-Methylglutaryl Coenzyme A Reductase on Squalene Synthesis in *Saccharomyces cerevisiae*," Applied and Environmental Microbiology, vol. 63, No. 9, Sep. 1997, pp. 3341-3344.
Hansen et al., "terpene synthase [Tripterygium wilfordii]," GenBank, APD77393.1, Nov. 28, 2016, 1 page.
Hansen et al., "Tripterygium wilfordii terpene synthase 12 (TPS12) mRNA, complete cds," GenBank, KY193788.1, Nov. 28, 2016, 1 page.
Jakočiūnas et al., "Multiplex Metabolic Pathway Engineering using CRISPR/Cas9 in *Saccharomyces cerevisiae*," Metabolic Engineering, vol. 28, 2015, (Available online Jan. 28, 2015), pp. 213-222.
Rodriguez et al., "Production and Quantification of Sesquiterpenes in *Saccharomyces cerevisiae*, including Extraction, Detection and Quantification of Terpene Products and Key Related Metabolites," Nature Protocols, vol. 9, No. 8, 2014, pp. 1980-1996.
Tong et al., "Eudesmane-type Sesquiterpene Diols Directly Synthesized by a Sesquiterpene Cyclase in Tripterygium wilfordii," Biochemical Journal, vol. 475, 2018 (Version of Record published: Sep. 5, 2018), pp. 2713-2725.
Zhou et al., "Modular Pathway Engineering of Diterpenoid Synthases and the Mevalonic Acid Pathway for Miltiradiene Production," Journal of the American Chemical Society, vol. 134, 2012 (Published: Jan. 26, 2012), pp. 3234-3241.

*Primary Examiner* — Tekchand Saidha
(74) *Attorney, Agent, or Firm* — Birch, Stewart, Kolasch & Birch, LLP

(57) ABSTRACT

Provided are a Cryptomeridiol synthase and a coding gene thereof. Also provided are a Cryptomeridiol synthase and a coding gene, a engineered yeast containing the Cryptomeridiol coding gene, and a use of same in plant breeding and biosynthesis. The cDNA full-length sequence of the Cryptomeridiol synthase gene in *Tripterygium wilfordii* is obtained by means of polymerase chain reaction cloning. Then, by means of synthetic biology, the engineered yeast containing the Cryptomeridiol synthase gene is constructed to realize the production of Cryptomeridiol in the yeast.

10 Claims, 2 Drawing Sheets

Specification includes a Sequence Listing.

SEQUENCE LISTING

<160> NUMBER OF SEQ ID NOS: 44

<210> SEQ ID NO 1
<211> LENGTH: 1662
<212> TYPE: DNA
<213> ORGANISM: Tripterygium wilfordii

<400> SEQUENCE: 1

-continued

```
atggcagcga ccacccaatc cacggaggct ccacggcggt tggccaactt cgcccctgcc    60
gtttggggtc acgatgactt tgcttctttt gcttctgatc aagattcgga gtacggatcg   120
tacacaaaga tagtggagga gttgaaagta caagtgaaag atatgttgtt gtctacaaat   180
gagattgtgg agaaagttga gttgattgac ttgttgggtc gtcttggtat ttcatatcac   240
tttgaaagtg aaattgaaga ccagcttatg caaaatctcg acatagtcaa aactaaactc   300
gtggatgaca acaatgacta cggcctatac gccgttgcac ttctgttccg cgtcttcaga   360
caacatggtt gcaaaatttc ttgtgatgtg tttgacaaat ttaagggaga tgatggaaag   420
ttgaaaatga gtctagctag tgatgtagag gggatgctaa gcttgtacga agcttctcac   480
ttgagcatgc atggagagga tgttttggat gaagcacttg gttttcaaa aacttctctt   540
cattccgcgg tgacccaatt gaacccacac tttgcaaacc aagttgccca tgcattgcaa   600
caaccttatc aaaagggcat tccaagaatc gagtcaaggc aatacatcaa tttctatgaa   660
gaggacgagt ctcggaatga aattctgctc aaattagcga aaatcgattt taatcgagta   720
caattgttgc accaacaaga gctaagtcat gtctcaaggt ggtataaaga cttgcagatt   780
gcttcaaaat ttccttatgc aagagacaga attgctgaaa tctatatgtg gactgttggg   840
tctaactttg aaccacatta tggacgtgtc cgaatctttc ttactaaaag tgtgacaatg   900
atatcaattt tagacgacac atacgatgct acggtacaa ttgaagaact tcgactcttg   960
actgatgcaa tagataggtg ggacattggt gccattgatc aattaccaga ttacatgaaa  1020
gttctttaca agatgattct aaatctctac gatgaattcg agaacgaatt gaaaaacgaa  1080
ggaagatctt cctgtgttgc ttatgctaga gacgcgttaa gagaaatggt gaaagcctac  1140
cacgttgaag ctgagtggtg caacaaaagt tacgtaccaa cattcgatga gtacatggag  1200
aatgcactga tcacaagctg ttatcatgca attccagctg catgttttct aggcatggga  1260
gaaattgcag ggataaaaga atttgaatgg ctcaaaagca tcccgaaaat ggttagggct  1320
tccgagatga tcggtcgtct tatggacgac ataatgtcac ataaggagga acaaaagagg  1380
gggcatgttg cctcaagcgt tgagtgcttt atgaagcaat atggtgtgtc agaagaagag  1440
gtggttaaag atttccaaaa cagggttgcg aatgcatgga aggatattaa tgaagagtgt  1500
atgagaccaa ctgctgtgtc tcttcatctt ctgatgccaa ttctgaacct aacacgcatc  1560
atcgatgttg tctacaagaa cgacgatggg tattcaaatc cagtcaattt gaaggagcat  1620
gtcaagtctt tgttcattca acaaatacca atgcaagatt aa                     1662
```

<210> SEQ ID NO 2
<211> LENGTH: 553
<212> TYPE: PRT
<213> ORGANISM: Tripterygium wilfordii

<400> SEQUENCE: 2

```
Met Ala Ala Thr Thr Gln Ser Thr Glu Ala Pro Arg Arg Leu Ala Asn
1               5                  10                  15

Phe Ala Pro Ala Val Trp Gly His Asp Asp Phe Ala Ser Phe Ala Ser
            20                  25                  30

Asp Gln Asp Ser Glu Tyr Gly Ser Tyr Thr Lys Ile Val Glu Glu Leu
        35                  40                  45

Lys Val Gln Val Lys Asp Met Leu Leu Ser Thr Asn Glu Ile Val Glu
    50                  55                  60

Lys Val Glu Leu Ile Asp Leu Leu Gly Arg Leu Gly Ile Ser Tyr His
65                  70                  75                  80
```

-continued

```
Phe Glu Ser Glu Ile Glu Asp Gln Leu Met Gln Asn Leu Asp Ile Val
                 85                  90                  95

Lys Thr Lys Leu Val Asp Asp Asn Asp Tyr Gly Leu Tyr Ala Val
            100                 105                 110

Ala Leu Leu Phe Arg Val Phe Arg Gln His Gly Cys Lys Ile Ser Cys
            115                 120                 125

Asp Val Phe Asp Lys Phe Lys Gly Asp Asp Gly Lys Leu Lys Met Ser
130                 135                 140

Leu Ala Ser Asp Val Glu Gly Met Leu Ser Leu Tyr Glu Ala Ser His
145                 150                 155                 160

Leu Ser Met His Gly Glu Asp Val Leu Asp Glu Ala Leu Gly Phe Ser
                165                 170                 175

Lys Thr Ser Leu His Ser Ala Val Thr Gln Leu Asn Pro His Phe Ala
            180                 185                 190

Asn Gln Val Ala His Ala Leu Gln Gln Pro Tyr Gln Lys Gly Ile Pro
            195                 200                 205

Arg Ile Glu Ser Arg Gln Tyr Ile Asn Phe Tyr Glu Glu Asp Glu Ser
            210                 215                 220

Arg Asn Glu Ile Leu Leu Lys Leu Ala Lys Ile Asp Phe Asn Arg Val
225                 230                 235                 240

Gln Leu Leu His Gln Gln Glu Leu Ser His Val Ser Arg Trp Tyr Lys
                245                 250                 255

Asp Leu Gln Ile Ala Ser Lys Phe Pro Tyr Ala Arg Asp Arg Ile Ala
                260                 265                 270

Glu Ile Tyr Met Trp Thr Val Gly Ser Asn Phe Glu Pro His Tyr Gly
            275                 280                 285

Arg Val Arg Ile Phe Leu Thr Lys Ser Val Thr Met Ile Ser Ile Leu
290                 295                 300

Asp Asp Thr Tyr Asp Ala Tyr Gly Thr Ile Glu Glu Leu Arg Leu Leu
305                 310                 315                 320

Thr Asp Ala Ile Asp Arg Trp Asp Ile Gly Ala Ile Asp Gln Leu Pro
                325                 330                 335

Asp Tyr Met Lys Val Leu Tyr Lys Met Ile Leu Asn Leu Tyr Asp Glu
            340                 345                 350

Phe Glu Asn Glu Leu Lys Asn Glu Gly Arg Ser Ser Cys Val Ala Tyr
            355                 360                 365

Ala Arg Asp Ala Leu Arg Glu Met Val Lys Ala Tyr His Val Glu Ala
370                 375                 380

Glu Trp Cys Asn Lys Ser Tyr Val Pro Thr Phe Asp Glu Tyr Met Glu
385                 390                 395                 400

Asn Ala Leu Ile Thr Ser Cys Tyr His Ala Ile Pro Ala Ala Cys Phe
                405                 410                 415

Leu Gly Met Gly Glu Ile Ala Gly Ile Lys Glu Phe Glu Trp Leu Lys
                420                 425                 430

Ser Ile Pro Lys Met Val Arg Ala Ser Glu Met Ile Gly Arg Leu Met
            435                 440                 445

Asp Asp Ile Met Ser His Lys Glu Glu Gln Lys Arg Gly His Val Ala
450                 455                 460

Ser Ser Val Glu Cys Phe Met Lys Gln Tyr Gly Val Ser Glu Glu Glu
465                 470                 475                 480

Val Val Lys Asp Phe Gln Asn Arg Val Ala Asn Ala Trp Lys Asp Ile
            485                 490                 495
```

```
Asn Glu Glu Cys Met Arg Pro Thr Ala Val Ser Leu His Leu Leu Met
            500                 505                 510

Pro Ile Leu Asn Leu Thr Arg Ile Ile Asp Val Val Tyr Lys Asn Asp
        515                 520                 525

Asp Gly Tyr Ser Asn Pro Val Asn Leu Lys Glu His Val Lys Ser Leu
    530                 535                 540

Phe Ile Gln Gln Ile Pro Met Gln Asp
545                 550

<210> SEQ ID NO 3
<211> LENGTH: 24
<212> TYPE: DNA
<213> ORGANISM: Human adenovirus type 1

<400> SEQUENCE: 3
gtaccgtaag catcgtatgt gtcg                                              24

<210> SEQ ID NO 4
<211> LENGTH: 22
<212> TYPE: DNA
<213> ORGANISM: Human adenovirus type 1

<400> SEQUENCE: 4
ctatgaagag gacgagtctc gg                                                22

<210> SEQ ID NO 5
<211> LENGTH: 23
<212> TYPE: DNA
<213> ORGANISM: Human adenovirus type 1

<400> SEQUENCE: 5
atggcagcga ccacccaatc cac                                               23

<210> SEQ ID NO 6
<211> LENGTH: 24
<212> TYPE: DNA
<213> ORGANISM: Human adenovirus type 1

<400> SEQUENCE: 6
ttaatcttgc attggtattt gttg                                              24

<210> SEQ ID NO 7
<211> LENGTH: 23
<212> TYPE: DNA
<213> ORGANISM: Human adenovirus type 1

<400> SEQUENCE: 7
atagcttcaa aatgtttcta ctc                                               23

<210> SEQ ID NO 8
<211> LENGTH: 23
<212> TYPE: DNA
<213> ORGANISM: Human adenovirus type 1

<400> SEQUENCE: 8
tttgtaatta aaacttagat tag                                               23

<210> SEQ ID NO 9
<211> LENGTH: 24
<212> TYPE: DNA
<213> ORGANISM: Human adenovirus type 1

<400> SEQUENCE: 9
```

```
gttaattcaa attaattgat atag                                          24

<210> SEQ ID NO 10
<211> LENGTH: 23
<212> TYPE: DNA
<213> ORGANISM: Human adenovirus type 1

<400> SEQUENCE: 10
agtaagctac tatgaaagac ttt                                           23

<210> SEQ ID NO 11
<211> LENGTH: 23
<212> TYPE: DNA
<213> ORGANISM: Human adenovirus type 1

<400> SEQUENCE: 11
gaattgggga tctacgtatg gtc                                           23

<210> SEQ ID NO 12
<211> LENGTH: 21
<212> TYPE: DNA
<213> ORGANISM: Human adenovirus type 1

<400> SEQUENCE: 12
agtttatgta tgtgttttt g                                              21

<210> SEQ ID NO 13
<211> LENGTH: 23
<212> TYPE: DNA
<213> ORGANISM: Human adenovirus type 1

<400> SEQUENCE: 13
gaattgggga tctacgtatg gtc                                           23

<210> SEQ ID NO 14
<211> LENGTH: 25
<212> TYPE: DNA
<213> ORGANISM: Human adenovirus type 1

<400> SEQUENCE: 14
tgccgtaaac cactaaatcg gaacc                                         25

<210> SEQ ID NO 15
<211> LENGTH: 23
<212> TYPE: DNA
<213> ORGANISM: Human adenovirus type 1

<400> SEQUENCE: 15
atggcttcag aaaagaaat tag                                            23

<210> SEQ ID NO 16
<211> LENGTH: 21
<212> TYPE: DNA
<213> ORGANISM: Human adenovirus type 1

<400> SEQUENCE: 16
ctatttgctt ctcttgtaaa c                                             21

<210> SEQ ID NO 17
<211> LENGTH: 25
<212> TYPE: DNA
<213> ORGANISM: Human adenovirus type 1
```

<400> SEQUENCE: 17
atgactgccg acaacaatag tatgc                                        25

<210> SEQ ID NO 18
<211> LENGTH: 25
<212> TYPE: DNA
<213> ORGANISM: Human adenovirus type 1

<400> SEQUENCE: 18
ttatagcatt ctatgaattt gcctg                                        25

<210> SEQ ID NO 19
<211> LENGTH: 35
<212> TYPE: DNA
<213> ORGANISM: Human adenovirus type 1

<400> SEQUENCE: 19
acaggatctt aatagacgaa gttttagagc tagaa                             35

<210> SEQ ID NO 20
<211> LENGTH: 35
<212> TYPE: DNA
<213> ORGANISM: Human adenovirus type 1

<400> SEQUENCE: 20
ttttccactg cactttgcat gttttagagc tagaa                             35

<210> SEQ ID NO 21
<211> LENGTH: 36
<212> TYPE: DNA
<213> ORGANISM: Human adenovirus type 1

<400> SEQUENCE: 21
gtcacacctg catcggatca tttatctttc actgcg                            36

<210> SEQ ID NO 22
<211> LENGTH: 36
<212> TYPE: DNA
<213> ORGANISM: Human adenovirus type 1

<400> SEQUENCE: 22
cttgcacctg catcggtttt agagctagaa atagca                            36

<210> SEQ ID NO 23
<211> LENGTH: 24
<212> TYPE: DNA
<213> ORGANISM: Human adenovirus type 1

<400> SEQUENCE: 23
gatcttttcc actgcacttt gcat                                         24

<210> SEQ ID NO 24
<211> LENGTH: 24
<212> TYPE: DNA
<213> ORGANISM: Human adenovirus type 1

<400> SEQUENCE: 24
aaacatgcaa agtgcagtgg aaaa                                         24

<210> SEQ ID NO 25
<211> LENGTH: 24
<212> TYPE: DNA
<213> ORGANISM: Human adenovirus type 1

```
<400> SEQUENCE: 25
gatcacagga tcttaataga cgaa                                          24

<210> SEQ ID NO 26
<211> LENGTH: 24
<212> TYPE: DNA
<213> ORGANISM: Human adenovirus type 1

<400> SEQUENCE: 26
aaacttcgtc tattaagatc ctgt                                          24

<210> SEQ ID NO 27
<211> LENGTH: 120
<212> TYPE: DNA
<213> ORGANISM: Human adenovirus type 1

<400> SEQUENCE: 27
cattattcca gaaaatacta atacttcttc acacaaaaga acgcagttag acaatcaaca   60
tttttttttt ccatttcttc tttccgttat attatattat actatattcc ctttaactaa  120

<210> SEQ ID NO 28
<211> LENGTH: 120
<212> TYPE: DNA
<213> ORGANISM: Human adenovirus type 1

<400> SEQUENCE: 28
ttagttaaag ggaatatagt ataatataat ataacggaaa gaagaaatgg aaaaaaaaaa   60
tgttgattgt ctaactgcgt tcttttgtgt gaagaagtat tagtattttc tggaataatg  120

<210> SEQ ID NO 29
<211> LENGTH: 298
<212> TYPE: DNA
<213> ORGANISM: Human adenovirus type 1

<400> SEQUENCE: 29
ctagagaccc tgcgagcgtg tcccggtggg ttctgggagc tctaactccg caggaactac   60
aaaccttgct tacacagagt gaacctgctg cctggcgtgc tctgactcag tacatttcat  120
agcccatctt caacaacaat accgacttca tcagaatgcg ttatcggttt tgggtttagt  180
gcctaaacga gcagcgagaa cacgaccacg ggctatataa atggaaagtt aggacagggg  240
caaagaataa gagcacagaa gaagagaaaa gacgaagagc agaagcggaa aacgtata    298

<210> SEQ ID NO 30
<211> LENGTH: 22
<212> TYPE: DNA
<213> ORGANISM: Human adenovirus type 1

<400> SEQUENCE: 30
ctagagaccc tgcgagcgtg tc                                            22

<210> SEQ ID NO 31
<211> LENGTH: 25
<212> TYPE: DNA
<213> ORGANISM: Human adenovirus type 1

<400> SEQUENCE: 31
tatacgtttt ccgcttctgc tcttc                                         25

<210> SEQ ID NO 32
```

<210> SEQ ID NO 32
<211> LENGTH: 38
<212> TYPE: DNA
<213> ORGANISM: Human adenovirus type 1

<400> SEQUENCE: 32
atagcttgtc accttacgta caatcttgat ccggagct                    38

<210> SEQ ID NO 33
<211> LENGTH: 35
<212> TYPE: DNA
<213> ORGANISM: Human adenovirus type 1

<400> SEQUENCE: 33
cttaggggca gacatactcc aagctgcctt tgtgt                       35

<210> SEQ ID NO 34
<211> LENGTH: 35
<212> TYPE: DNA
<213> ORGANISM: Human adenovirus type 1

<400> SEQUENCE: 34
aaggcagctt ggagtatgtc tgcccctaag aagat                       35

<210> SEQ ID NO 35
<211> LENGTH: 41
<212> TYPE: DNA
<213> ORGANISM: Human adenovirus type 1

<400> SEQUENCE: 35
tactactcag taataactta agcaaggatt ttcttaactt c                41

<210> SEQ ID NO 36
<211> LENGTH: 39
<212> TYPE: DNA
<213> ORGANISM: Human adenovirus type 1

<400> SEQUENCE: 36
agaaaatcct tgcttaagtt attactgagt agtatttat                   39

<210> SEQ ID NO 37
<211> LENGTH: 35
<212> TYPE: DNA
<213> ORGANISM: Human adenovirus type 1

<400> SEQUENCE: 37
agggtgatgg ttcacgtagt gggccatcgc cctga                       35

<210> SEQ ID NO 38
<211> LENGTH: 23
<212> TYPE: DNA
<213> ORGANISM: Human adenovirus type 1

<400> SEQUENCE: 38
gcaccataaa cgacattact ata                                    23

<210> SEQ ID NO 39
<211> LENGTH: 21
<212> TYPE: DNA
<213> ORGANISM: Human adenovirus type 1

<400> SEQUENCE: 39
accccaaaaa acttgattag g                                      21

<210> SEQ ID NO 40
<211> LENGTH: 20
<212> TYPE: DNA
<213> ORGANISM: Human adenovirus type 1

<400> SEQUENCE: 40
tcctcgtatt gtcttgccgg                                              20

<210> SEQ ID NO 41
<211> LENGTH: 20
<212> TYPE: DNA
<213> ORGANISM: Human adenovirus type 1

<400> SEQUENCE: 41
ctagaccacc tgcgcctaac                                              20

<210> SEQ ID NO 42
<211> LENGTH: 20
<212> TYPE: DNA
<213> ORGANISM: Human adenovirus type 1

<400> SEQUENCE: 42
ctagagaccc tgcgagcgtg                                              20

<210> SEQ ID NO 43
<211> LENGTH: 20
<212> TYPE: DNA
<213> ORGANISM: Human adenovirus type 1

<400> SEQUENCE: 43
cagctacgta gtgacagtac                                              20

<210> SEQ ID NO 44
<211> LENGTH: 527
<212> TYPE: PRT
<213> ORGANISM: Saccharomyces cerevisiae

<400> SEQUENCE: 44

Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175

```
Thr Ser Tyr His Ile Pro Met Ala Thr Thr Glu Gly Cys Leu Val Ala
            180             185             190

Ser Ala Met Arg Gly Cys Lys Ala Ile Asn Ala Gly Gly Ala Thr
        195             200             205

Thr Val Leu Thr Lys Asp Gly Met Thr Arg Gly Pro Val Val Arg Phe
        210             215             220

Pro Thr Leu Lys Arg Ser Gly Ala Cys Lys Ile Trp Leu Asp Ser Glu
225             230             235             240

Glu Gly Gln Asn Ala Ile Lys Lys Ala Phe Asn Ser Thr Ser Arg Phe
                245             250             255

Ala Arg Leu Gln His Ile Gln Thr Cys Leu Ala Gly Asp Leu Leu Phe
            260             265             270

Met Arg Phe Arg Thr Thr Thr Gly Asp Ala Met Gly Met Asn Met Ile
            275             280             285

Ser Lys Gly Val Glu Tyr Ser Leu Lys Gln Met Val Glu Glu Tyr Gly
        290             295             300

Trp Glu Asp Met Glu Val Val Ser Val Ser Gly Asn Tyr Cys Thr Asp
305             310             315             320

Lys Lys Pro Ala Ala Ile Asn Trp Ile Glu Gly Arg Gly Lys Ser Val
                325             330             335

Val Ala Glu Ala Thr Ile Pro Gly Asp Val Val Arg Lys Val Leu Lys
            340             345             350

Ser Asp Val Ser Ala Leu Val Glu Leu Asn Ile Ala Lys Asn Leu Val
            355             360             365

Gly Ser Ala Met Ala Gly Ser Val Gly Gly Phe Asn Ala His Ala Ala
        370             375             380

Asn Leu Val Thr Ala Val Phe Leu Ala Leu Gly Gln Asp Pro Ala Gln
385             390             395             400

Asn Val Glu Ser Ser Asn Cys Ile Thr Leu Met Lys Glu Val Asp Gly
                405             410             415

Asp Leu Arg Ile Ser Val Ser Met Pro Ser Ile Glu Val Gly Thr Ile
            420             425             430

Gly Gly Gly Thr Val Leu Glu Pro Gln Gly Ala Met Leu Asp Leu Leu
        435             440             445

Gly Val Arg Gly Pro His Ala Thr Ala Pro Gly Thr Asn Ala Arg Gln
        450             455             460

Leu Ala Arg Ile Val Ala Cys Ala Val Leu Ala Gly Glu Leu Ser Leu
465             470             475             480

Cys Ala Ala Leu Ala Ala Gly His Leu Val Gln Ser His Met Thr His
                485             490             495

Asn Arg Lys Pro Ala Glu Pro Thr Lys Pro Asn Asn Leu Asp Ala Thr
            500             505             510

Asp Ile Asn Arg Leu Lys Asp Gly Ser Val Thr Cys Ile Lys Ser
            515             520             525
```

TRIPTERYGIUM WILFORDII CRYPTOMERIDIOL SYNTHASE, CODING GENE THEREOF AND RECOMBINANT YEAST CONTAINING CODING GENE

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "6256-0111PUSi_ST25.txt" created on Feb. 1, 2021 and is 17,203 bytes in size. The sequence listing contained in this .txt file is part of the specification and is hereby incorporated by reference herein in its entirety.

TECHNICAL FIELD OF THE INVENTION

Embodiments of the invention relate to cryptomeridiol synthase and its coding gene, and recombinant yeast containing the coding gene of the cryptomeridiol synthase, belongs to a field of synthetic biology of medicinal ingredients.

A full-length cDNA sequence of a new cryptomeridiol synthase gene (TwCS) in *Tripterygium wilfordii* Hook.F was obtained from cloning for the first time by polymerase chain reaction, and then synthetic biological methods were used to construct yeast engineered bacteria, and product cryptomeridiol in yeast.

BACKGROUND OF THE INVENTION

Sesquiterpene compounds are a kind of natural compounds with a variety of physiological and ecological functions, such as anti-microbial, defense against insects and herbivores, and so on. Currently, large amount of sesquiterpene compounds are found in both higher and lower classes of plants, and widely used in the fields of industry, agriculture and medicine. Biosynthesis of sesquiterpenes only originated from simple C5 isoprene structural unit, isopentenyl pyrophosphate (IPP) and its isomer dimethylallyl pyrophosphate (DMAPP). Trimolecular C5 unit is subjected to a cascade reaction with participation of isopentenyl transferase, carbon chain is extended, to form farnesyl pyrophosphate (FPP) containing 15 carbon atoms, FPP can then be cyclized to form sesquiterpenes with various structures under the catalysis of sesquiterpene synthase.

Cryptomeridiol was first found in *Cryptomeria japonica* plants, and then was detected with small amount from volatile oils of various plants. Cryptomeridiol has a certain antispasmodic effect and is active ingredient of antispasmodic drug Proximol®. Since there is low amount of cryptomeridiol in plants and it is difficult for separation of cryptomeridiol, some researchers designed ways of chemical synthesis and semi-synthesis thereof such as metal ion-catalyzed oxidation, in which cryptomeridiol can be synthesized by multi-step reaction of (−)-elemol. In addition, ilicic acid can be used as starting material, then a relatively simple and efficient semi-synthetic process can be used to obtain cryptomeridiol by three steps of reaction.

However, the use of multi-step synthesis steps is more complex than ways of the synthesis of cryptomeridiol in plants involving enzymes. At present, microbial fermentation through cell factories is highly competitive in the industrial production of monomer compounds. Gene elements (promoter, transcriptional regulatory region, ribosome binding site, open reading frame, terminator, etc.) are organically reconstructed and linked to form a functional gene module according to the needs for the engineering object. By using existing biological network while introducing new functional gene modules, such product can be expressed, in which the product can not be synthesized by natural cells, or with very low content. If complete biosynthesis way for artemisinic acid is used to produce artemisinin as antimalarial drug in yeast engineered bacteria, 25 grams of artemisinic acid can be produced per liter of fermentation broth.

SUMMARY OF THE INVENTION

An embodiment of the invention provides a cryptomeridiol synthase, with the following amino acid sequence:
(1) amino acid sequence as SEQ ID NO:2.
(2) amino acid sequence resulted from the amino acid sequence as SEQ ID NO:2 being substituted, deleted or added with one or more amino acids, with same function of protein.

An embodiment of the invention provides gene encoding the cryptomeridiol synthase (*Tripterygium wilfordii* cryptomeridiol synthase, TwCS), wherein the gene is at least one of following:
(1) nucleotide molecule shown in SEQ ID NO:1;
(2) nucleotide sequence resulted from the nucleotide molecule shown in SEQ ID NO:1 being substituted, deleted or added with one or more nucleotide, with expressing same function of protein;
(3) nucleotide sequence hybridized with the nucleotide molecules shown in SEQ ID NO:1 under stringent conditions, the stringent conditions are that hybridizing in 0.1× SSPE solution containing 0.1% of SDS or 0.1×SSC solution containing 0.1% of SDS.

The term of "stringency" of the hybridization reaction can be easily determined by a person of ordinary skill in the art, and is usually calculated empirically based on the probe length, washing temperature, and salt concentration. Generally, longer probes require higher temperatures to anneal properly, while shorter probes require lower temperatures. Hybridization generally relies on the ability of denatured DNA to reanneal when the complementary strand is present in an environment below its melting temperature. The higher the degree of desired homology between the probe and the hybridizable sequence, the higher the relative temperature that can be used. As a result, it is inferred that higher relative temperatures will tend to make the reaction conditions more stringent, while lower temperatures are less stringent. For additional details and explanations on the stringency of hybridization reactions, see Ausubel et al., "Current Protocols in Molecular Biology", Wiley Interscience Publishers, 1995.

"Stringent conditions" or "Highly stringent conditions", as defined here, can be identified as follows: (1) washing with low ionic strength and high temperature, such as 0.015M sodium chloride/0.0015M sodium citrate/0.1% sodium lauryl sulphate, 50° C.; (2) during hybridization using denaturants such as formamide, e.g., 50% (v/v) formamide and 0.1% bovine serum albumin/0.1% Ficoll/0.1% polyethylene pyrrolidone/50 mM sodium phosphate buffer of pH 6.5, containing 750 mM sodium chloride, 75 mM sodium citrate, 42° C.; or (3) using 50% formamide, 5×SSC (0.75M NaCl, 0.075M sodium citrate), 50 mM Sodium phosphate (pH 6.8), 0.1% sodium pyrophosphate, 5×Denhardt's solution, sonicated salmon essence DNA (50 μg/ml), 0.1% SDS, and 10% dextran sulfate solution were hybridized overnight at 42° C., and washing in 0.2×SSC (sodium chloride/sodium citrate) at 42° C. for 10 minutes, followed by high stringency washing in 0.1×SSC with EDTA at 55° C. for 10 minutes.

An embodiment of the invention provides a recombinant expression vector, comprising a promoter, gene encoding the cryptomeridiol synthase, and a transcription terminator. The expression vector is obtained from splicing the promoter, the gene encoding the cryptomeridiol synthase, the terminator, and episomal vector by using a method of yeast homologous recombination, and the episomal vector is a yeast expression vector, such as pYX212, pYES2.0, pRS425, pRS426 or p424.

According to an embodiment of the invention, the vector is any one of the following:

(1) recombinant expression vector pYX212-TwCS, which contains promoter TPIp, cryptomeridiol synthase expression gene TwCS and terminator pYX121;

(2) recombinant expression vector pYX212-ERG20+TwCS, which contains promoter TPIp, EGR20 gene sequence, yeast terminator FBA1t, yeast promoter TEF1p, cryptomeridiol synthase expression gene TwCS and terminator pYX12t;

(3) recombinant expression vector pYX212-IDI+TwCS, which promoter TPIp, IDI gene, yeast terminator FBA1t, yeast promoter TEF1p, cryptomeridiol synthase expression gene TwCS and terminator pYX121;

(4) recombinant expression vector pYX212-(IDI-EGR20)+TwCS, which contains promoter TPIp, IDI gene, fusion protein linker peptide, EGR20 gene, yeast terminator FBA1t, yeast promoter TEF1p, cryptomeridiol synthase expression gene TwCS and terminator pYX21;

(5) recombinant expression vector pYX212-(EGR20-IDI)+TwCS, which contains promoter TPIp, EGR20 gene sequence, fusion protein linker peptide, IDI gene, yeast terminator FBA1t, yeast promoter TEF1p, cryptomeridiol synthase expression gene TwCS and terminator pYX12t;

wherein the fusion protein is any one of GGGS (SEQ ID NO: 44), GSG, GSGGGGS (SEQ ID NO: 45), GSGEAAAK (SEQ ID NO: 46), GSGEAAAKEAAAK (SEQ ID NO: 47) and GSGMGSSSN (SEQ ID NO: 48), preferably the GGGS (SEQ ID NO: 44) with coding gene sequence of ggtggtggttct (SEQ ID NO: 49).

An embodiment of the invention provides an engineered bacteria comprising the expression vector, the engineered bacteria may be selected from yeast cells or plant cells, preferably yeast cells, which may be GEN.PK series of *Saccharomyces cerevisiae* or BY series of *Saccharomyces cerevisiae*, such as BY4741 *Saccharomyces cerevisiae*.

An embodiment of the invention provides a building method for the engineered bacteria comprises:

(1) transforming recombinant expression vector pYX212-TwCS into yeast BY4741 strain to obtain engineering strain TE1; or (2) transforming recombinant expression vector pYX212-ERG20+TwCS into yeast BY4741 strain to obtain engineered strain TE2; or (3) transforming recombinant expression vector pYX212-IDI+TwCS into yeast BY4741 strain to obtain engineered strain TE3; or (4) transforming recombinant expression vector pYX212-(IDI-EGR20)+TwCS into yeast BY4741 strain to obtain engineered strain TE4; or (5) transforming recombinant expression vector pYX212-(EGR20-IDI)+TwCS into yeast BY4741 strain to obtain engineered strain TE5; or (6) transforming recombinant expression vector pYX212-(EGR20-IDI)+TwCS and the recombinant expression vector p424-tHMG1 into the yeast BY4741 strain to obtain engineered strain TE6; or (7) transforming recombinant expression vector pYX212-IDI+TwCS and the recombinant expression vector p424-tHMG1 into the yeast BY4741 strain to obtain engineered strain TE7;

wherein the recombinant expression vector p424-tHMG1 includes yeast promoter TDH3p, truncated HMG-CoA reductase gene tHMG1, yeast terminator TDH3t.

In order to obtain a higher expression level of cryptomeridiol in yeast, another embodiment of the present invention provides a more efficient engineered bacteria, i.e. recombinant yeast, which comprises the gene encoding the cryptomeridiol, and at least one of erg9 and rox1 genes is knocked out therefrom.

A preferred way is to knock out the erg9 gene in the recombinant yeast, more preferably, both of the erg9 gene and the rox1 gene are knocked out.

The more efficient recombinant yeast expressing cryptomeridiol includes at least the following gene fragments:

recombinant expression vector pYX212-IDI+TwCS, which is constructed from promoter TPIp, IDI gene, yeast terminator FBA1t, yeast promoter TEF1p, cryptomeridiol synthase expression gene TwCS, and terminator pYX12t into plasmid pYX212;

recombinant expression vector p424-tHMG1, which is constructed from yeast promoter TDH3p, truncated HMG-COA reductase gene tHMG1, yeast terminator TDH3t into plasmid p424.

The more efficient recombinant yeast expressing cryptomeridiol is constructed by following steps:

(1) constructing mutant strains: knocking out the erg9 gene in the BY4741 yeast strain, to obtain mutant strain BY4741erg9::Δ-200--176; or knocking out the erg9 gene and the rox1 gene in the BY4741 yeast strain, to obtain mutant strain BY4741 erg9::Δ-200--176 rox1::mut;

(2) constructing recombinant expression vectors pYX212-IDI+TwCS and p424-tHMG1;

(3) transforming recombinant expression vectors pYX212-IDI+TwCS and p424-tHMG1 into the mutant strain BY4741 erg9::Δ-200--176, to obtain yeast engineering strain TE8; or transforming recombinant expression vectors pYX212-IDI+TwCS and p424-tHMG1 into the mutant yeast strain BY4741 erg9::Δ--200--176 rox1::mut to obtain the yeast engineering strain TE9.

Another embodiment of the invention provides application of the cryptomeridiol synthase, the coding gene of the cryptomeridiol synthase, the recombinant expression vector, or the engineered bacteria of embodiment of the invention, in synthesis of cryptomeridiol and eucalyptol. After 2 to 3 days of fermentation to get bacterial strain, fermentation broth was extracted with n-hexane, and could be detected by GC-MS, to obtain product of sesquiterpene, which is subjected to structural identification to be determined that main product is cryptomeridiol.

With embodiment of the invention, cryptomeridiol can be generated by biosynthesis technology, problem of lack of drug source can be alleviated, and embodiment of the invention has a good application prospect.

Another embodiment of the invention provides application of the cryptomeridiol synthase or the coding gene of the cryptomeridiol synthase in plant breeding containing the chemical composition of cryptomeridiol. With the cryptomeridiol synthase or its coding gene, content of cryptomeridiol in the plant can be improved by applying it to plant cells.

DETAILED DESCRIPTION OF THE INVENTION

Figure 1:
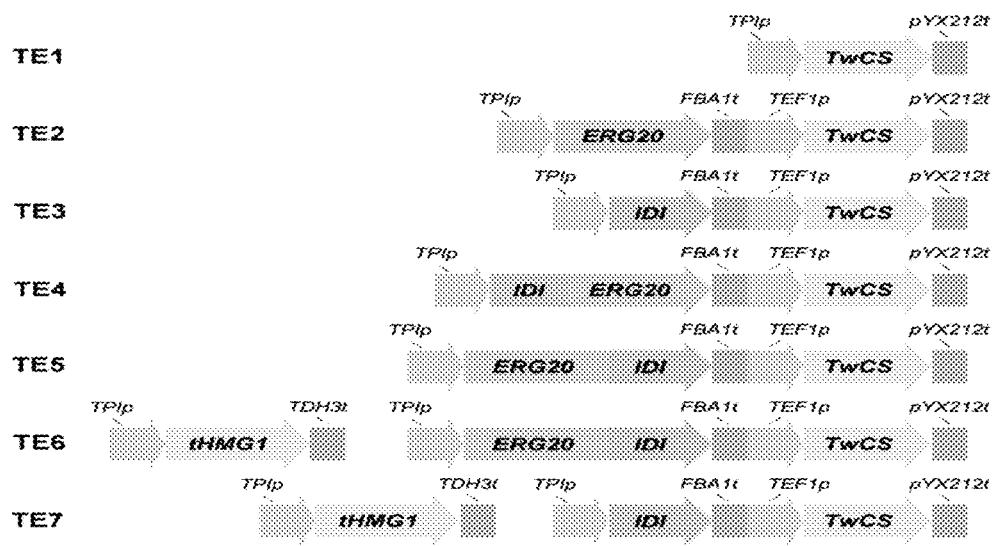
FIG. 1 is a brief diagram of plasmid type of TE1-TE7 strain.

Hereinafter, various aspects and features of embodiment of the invention will be described in detail through preferred embodiments in conjunction with the accompanying drawings. Those skilled in the art should understand that these embodiments are only for illustration, and do not limit the scope of embodiment of the invention. Without departing from the scope of the claims, those skilled in the art can make various modifications and improvements to various aspects of embodiment of the invention, and these modifications and improvements also fall within the protection scope of embodiment of the invention. For example, replacing the promoters and expression vectors used in the examples with other promoters and expression vectors commonly used in the art can be understood and realized by those of ordinary skill in the art.

The experimental methods used in the following examples are conventional methods unless otherwise specified.

Materials, reagents and so on used in following embodiments, unless otherwise specified, can be obtained from commercial sources. For example, both of p426-SNR52p-gRNA eukaryotic expression vector and p414-TEF1p-Cas9-CYC1t eukaryotic expression vector are bought from Addgene; pESC-LEU eukaryotic expression vector is purchased from Agilent Technologies; SC-His Yeast Medium, SC-Trp-His Yeast Medium, SC-URA-Trp-His Yeast Medium are all purchased from Beijing FunGenome Technology Ltd.

In quantitative tests of following embodiments, three times of repeating experiments are set, and results thereof are averaged.

*Tripterygium wilfordii* Hook.f. suspension cells in following embodiments was disclosed in "Cloning and expression analysis of 4-(cytidine-5-diphospho)-2-C-methyl-D-erythritol kinase gene in *Tripterygium wilfordii*", China Journal of Chinese Materia Medica, 1 Nov. 2015, 40(21):4165-4170, and the public can obtain it from the Laboratory of Molecular Biomedicine and Traditional Chinese Medicine Resources of Capital Medical University.

Embodiment 1: Total RNA Extraction and Purification of *Tripterygium wilfordii* Suspension Cells The total RNA of suspension cells of *Tripterygium wilfordii* was extracted by modified CTAB method (CTAB Buffer: 2% CTAB (W/V); 100 mmol·L−1Tris-HCl (pH 8.0); 25 mmol·L$^{-1}$ EDTA; 2.0 mol·L−1 NaC 0.5 g·L$^{-1}$ spermidine). RNA purification kit (Tiangen BioTech Co., Ltd.) was used to purify the RNA.

Embodiment 2: Full-Length cDNA Cloning of TwCS Gene

1. Primer Design

According to data annotation of *Tripterygium wilfordii* transcriptome, full-length gene sequence was screened, and the 5'RACE and 3'RACE primers were designed, sequence of which is as following:

```
5'RACE
                                    (SEQ ID NO: 3)
GTACCGTAAGCATCGTATGTGTCG

3'RACE
                                    (SEQ ID NO: 4)
CTATGAAGAGGACGAGTCTCGG
```

2. PCR Amplification

Using PrimeScript 1$^{st}$ Strand cDNA Synthesis Kit (from Takara Co.) kit, the RNA obtained in embodiment 1 was reverse transcribed into first strand cDNA of RACE Ready. Rapid amplification of the end of SMARTer™ RACE was carried out according to the instructions of cDNA kit.

The 3' and 5' ends of DNA sequence of SEQ ID No. 1 were obtained by the RACE method, and then primers were designed according to the sequence information, in which sequences of the primers are as follows:

```
TwCS-F
                                    (SEQ ID NO: 5)
ATGGCAGCGACCACCCAATCCAC

TwCS-R
                                    (SEQ ID NO: 6)
TTAATCTTGCATTGGTATTTGTTG
```

The first strand cDNA of RACE Ready was used as template for PCR amplification.

The PCR reaction conditions were 98° C. 30 s, 98° C. 10 s, 60° C. 15 s, 72° C. 1 min, 35 cycles and 72° C., 7 min.

Results of sequencing showed that sequence of PCR amplification product was as shown by SEQ ID No. 1, and gene shown in SEQ ID No. 1 was named TwCS.

This DNA sequence encodes protein composed of 553 amino acids, and the protein was named TwCS, with amino acid sequence of SEQ ID No. 2.

Embodiment 3: Construction of Plasmi

1. Cloning of Promoter and Terminator

Promoter and terminator used in the present embodiment are publicly available on SGD website (https://www.yeastgenome.org).

Total DNA of yeast BY4741 was extracted by yeast genome extraction kit (Tiangen BioTech Co., Ltd.). Then by using this DNA as a template, following primers were designed:

```
TEF1p-F
                                    (SEQ ID NO: 7)
ATAGCTTCAAAATGTTTCTACTC

TEF1p-R
                                    (SEQ ID NO: 8)
TTTGTAATTAAAACTTAGATTAG

FBA1t-F
                                    (SEQ ID NO: 9)
GTTAATTCAAATTAATTGATATAG

FBA1t-R
                                    (SEQ ID NO: 10)
AGTAAGCTACTATGAAAGACTTT
```

Promoter TEF1p (TEF1 SGD ID: S000006284) and terminator FBA1t (FBA1 SGD ID: S000001543) fragments were obtained by PCR amplification.

Using pYX212 plasmid as a template, promoter TPIp and terminator pYX2121 were obtained by PCR amplification (as in embodiment 2). Amplification primers are as follows:

```
TPIp-F
                                    (SEQ ID NO: 11)
GAATTGGGGATCTACGTATGGTC

TPIp-R
                                    (SEQ ID NO: 12)
AGTTTATGTATGTGTTTTTTG pYX212t-F
                                    (SEQ ID NO: 13)
GAATTGGGGATCTACGTATGGTC pYX212t-R
                                    (SEQ ID NO: 14)
TGCCGTAAACCACTAAATCGGAACC
```

2. Acquisition of EGR20 Gene (Yeast FPP and GPP Synthase Gene)

According to gene sequence of yeast EGR20 (SGD ID: S000003703), primers are designed as follows:

```
ERG20-F:
                                    (SEQ ID NO: 15)
ATGGCTTCAGAAAAAGAAATTAG

ERG20-R:
                                    (SEQ ID NO: 16)
CTATTTGCTTCTCTTGTAAAC
```

Gene sequence of the yeast EGR20 was obtained by PCR amplification (specific steps are same as those in embodiment 2).

3. Acquisition of IDI Gene

According to gene sequence of yeast IDI (SGD ID:S000006038), primers were designed as follows:

```
IDI-F:
                                    (SEQ ID NO: 17)
ATGACTGCCGACAACAATAGTATGC

IDI-R:
                                    (SEQ ID NO: 18)
TTATAGCATTCTATGAATTTGCCTG
```

Gene sequence of yeast IDI was obtained by PCR amplification (specific steps are same as those in embodiment 2).

4. Construction of Expression Module

Using PCR method, following modules were built:
TPIp-ERG20-FBA1t-TEF1p
TPIp-IDI-FBA1t-TEF1p
TPIp-IDI/ERG20-FBA1t-TEF1p
TPIp-ERG20/IDI-FBA1t-TEF1p
TEF1p-TwCS-pYX2121
TPIp-TwCS-pYX212t Construction method is as follows: (1) mixing DNA fragments: promoters, genes, terminators, promoters . . . are mixed according to molar ratio of 1:3:5:7:XX:7:5:3:1, in which amount of DNA with ratio portion of 1 is 50 to 100 ng/kb; (2) first step of PCR: using mixed DNA from (1) as a template and amplifying by PCR without adding primers, in which reaction conditions of PCR were 98° C. 30 s; 98° C. 10 s, 60° C. 15 s, 72° C. 1 min, 15 cycles; and 72° C. 7 min; (3) second step PCR: taking 2 μL of PCR product from (2) as a template, using forward primers of the initial promoter, terminal terminator or reverse primers of the promoter for PCR amplification (specific steps are same as those of embodiment 2); (4) using EZNA Gel Extraction Kit (from OMEGA co.), purifying the PCR product according to instruction manual; (5) purifying the product, according to instruction manual of pEASY-Blunt Simple Cloning Kit (from Beijing TransGen Biotech Co., Ltd.), which was linked, transformed, and identified by sequencing, to get corresponding module DNA.

There is a

```
                                    (SEQ ID NO: 44)
                GGGS
                                    (SEQ ID NO: 49)
                (GGT GGTGGT TCT
``` linker connection between IDI and ERG20.

5. Construction of plasmid by homologous recombination method Using the method of homologous recombination on yeast, constructed module was connected to expression vector pYX212, specific operations of which are as follows:

(1) digesting expression vector pYX212 by BamH I endonuclease (from NEB Co.).

| Enzyme digestion reaction system (50 μL system) | |
|---|---|
| 10 × Cutsmart Buffer | 5 μL |
| DNA | ≤1 μg |
| BamH I | 1 μL |
| adding ddH$_2$O to total volume | 50 μL |

After reaction at 37° C. for 2 h, agarose gel electrophoresis was used to purify digested products according to instruction manual of EZNA Gel Extraction Kit (from OMEGA Co.).

(2) mixing TPIp-TwCS-pYX212t module with linear expression vector pYX212 obtained in (1), in which molar concentration of the module was 100 ng/kb and molar concentration of the vector was 60-80 ng/kb, then co-electrotransformation was performed to make them transformed into yeast BY4741 competent state, under conditions of 2.5 kV, 25 μF and 200Ω (Bio-Rad Gene Pulsers).

The yeast BY4741 competent state was prepared by lithium acetate transformation method.

(3) *Saccharomyces cerevisiae* strains were cultured in their respective screening dropout medium for 2 to 3 days, 30° C. A single colony is picked, by using E.Z.N.A. Yeast Plasmid Mini Kit (from OMEGA co.), with reference to the instruction manual, to extract yeast plasmids.

(4) using plasmids from (3) as a template, screening was performed by PCR method, in which primers for screening were TPIp-F and pYX212t-R (refer to "1. Cloning of promoter and terminator"). After sequencing and identification, recombinant plasmid pYX212-TPIp-TwCS-pYX2121 was obtained, abbreviated as pYX212-TwCS.

(5) repeating the steps in (1) to (4), constructing TPIp-ERG20-FBA1t-TEF1p, TPIp-IDI-FBA1t-TEF1p, TPIp-IDI/ERG20-FBA1t-TEF1p, TPIp-ERG20/IDI-FBA1t-TEF1p, TEF1p-TwCS-pYX212t modules into vector pYX212 in turn, and obtaining following recombinant plasmids:

pYX212-TPIp-ERG20-FBA1t-TEF1p-TwCS-pYX212t, abbreviated as pYX212-ERG20+TwCS;

pYX212-TPIp-IDI-FBA1t-TEF1p-TwCS-pYX212t, abbreviated as pYX212-IDI+TwCS;

pYX212-TPIp-IDI/ERG20-FBA1t-TEF1p-TwCS-pYX212t, abbreviated as pYX212-(IDI-ERG20)+TwCS;

pYX212-TPIp-ERG20/IDI-FBA1t-TEF1p-TwCS-pYX212t, abbreviated as pYX212-(ERG20-IDI)+TwCS.

(6) plasmid p424-tHMG1 is obtained by constructing yeast promoter TDH3p, gene tHMG1, yeast terminator TDH31 into plasmid p424, carries HIS3marker. Detailed construction method can be found in "Zhou, Y. J.; Gao, W.; Rong, Q.; Jin, G.; Chu, H.; Liu, W.; Yang, W.; Zhu, Z.; Li, G.; Zhu, G. J. Am. Chem. Soc. 2012, 134, 3234-3241.", can be obtained according to literature records, and can also be obtain by the public from the Laboratory of Molecular Pharmacognosy and traditional Chinese Medicine Resources of Capital Medical University.

Embodiment 4: Modification of Yeast Strain (1) gRNA sequence: referring to paper "Jakoqiiangnas, T.; Bonde, I.; Herrg å rd, M.; Harrison, S. J.; Kristensen, M.; Pedersen, L. E.; Jensen, M. K.; Keasling, J. D. Metab. Eng. 2015, 28, 213-222.", gRNA sequences of rox1 and erg9 promoters were designed as follows:

```
rox1
                                   (SEQ ID NO: 19)
ACAGGATCTTAATAGACGAAGTTTTAGAGCTAGAA erg9p
                                   (SEQ ID NO: 20)
TTTCCACTGCACTTTGCATGTTTTAGAGCTAGAA
```

(2) Modification of gRNA Vector

P426-SNR52p-gRNA vector (from Addgene co.) was modified by inserting two opposite restriction sites AarI at the 20 bp single RNA site, sequences of the restriction sites are as follows:

```
AarI:
                                   (SEQ ID NO: 50)
5'...CACCTGC(N)4↑... 3'

(SEQ ID NO: 51)
3'...GTGGACG(N)8↑... 5'
```

Using PCR amplification method (specific steps are same as those in embodiment 2), primers thereof are as follows:

```
pU01-F
                                   (SEQ ID NO: 21)
GTCACACCTGCATCGGATCATTTATCTTTCACTGCG
```

```
pU01-R
                                   (SEQ ID NO: 22)
CTTGCACCTGCATCGGTTTTAGAGCTAGAAATAGCA
```

Content with underline is sequence of AarI restriction site.

p426-SNR52p-gRNA vector was constructed into a first-class general vector pTY-U01.

(3) Construction of Single gRNA (sgRNA) Vector gRNA site was designed as a 24 nt Oligo with a complementary sticky end to the vector to form a double strand under the annealing procedure. Sequence of Oligo is shown in a table below.

```
erg9p-F
                                   (SEQ ID NO: 23)
GATCTTTTCCACTGCACTTTGCAT erg9p-R
                                   (SEQ ID NO: 24)
AAACATGCAAAGTGCAGTGGAAAA
```

| system: | Annealing Buffer | 2 μL |
|---|---|---|
|  | Oligo-F | 9 μL |
|  | Oligo-R | 9 μL |
|  | Total | 20 μL |

Conditions: 95° C., 5 min; 95 to 25° C., −1° C./min, 71 cycles, 10° C. hold.

Golden Gate reaction was used for connection.

system: AarI 2 μL

10× Buffer AarI 2 μL

50× oligonucleotide (0.025 mM) 0.4 μL

T4 Ligase(HC) 1 μL

T4 Ligase Buffer 2 μL pTY-U0130 fmol

Annealing oligo 2 μL ddH$_2$Oup to 20 μL conditions: 37° C., 4 h; 50° C., 5 min; 80° C., 5 min; 4° C. hold The connection product was screened by transforming, positive cloning, and sample sequencing, to obtain erg9p-gRNA vector.

By repeating steps (1) to (3), gRNA of rox1 was inserted into the vector, in which gRNA sequence is as follows:

```
rox1-F
                                   (SEQ ID NO: 25)
GATCACAGGATCTTAATAGACGAA rox1-R
                                   (SEQ ID NO: 26)
AAACTTCGTCTATTAAGATCCTGT
``` erg9p-rox1-gRNA vector was obtained.

(4) Obtaining dsOligo dsOligo of rox1 gene was obtained by synthesizing 120 nt long-stranded Oligo, annealing to form DNA double strand, which was then purified by using EZNA Gel Extraction Kit (from OMEGA co.) with reference to the instruction manual.

Synthetic sequence is as follows:

```
rox1-Oligo-F
                                          (SEQ ID NO: 27)
CATTATTCCAGAAAATACTAATACTTCTTCACACAAAAGAACGCAGT
TAGACAATCAACATTTTTTTTTCCATTTCTTCTTTCCGTTATATTATA
TTATACTATATTCCCTTTAACTAA rox1-Oligo-R
                                          (SEQ ID NO: 28)
TTAGTTAAAGGGAATATAGTATAATATAATATAACGGAAAGAAGAA
ATGGAAAAAAAAAATGTTGATTGTCTAACTGCGTTCTTTTGTGTGAA
GAAGTATTAGTATTTTCTGGAATAATG
``` erg9p directly adopts a method of synthesizing double-stranded DNA (from Beijing RuiBiotech Co., Ltd.), and then dsOligo of erg9p can be obtained by amplification using PCR method. Oligo sequence and amplification primers are as follows:

```
erg9p-OLIGO:
                                          (SEQ ID NO: 29)
5'-CTAGAGACCCTGCGAGCGTGTCCCGGTGGGTTCTGGGAGCTCTAA

CTCCGCAGGAACTACAAACCTTGCTTACACAGAGTGAACCTGCTGCC

TGGCGTGCTCTGACTCAGTACATTTCATAGCCCATCTTCAACAACAA

TACCGACTTCATCAGAATGCGTTATCGGTTTTGGGTTTAGTGCCTAA

ACGAGCAGCGAGAACACGACCACGGGCTATATAAATGGAAAGTTAG

GACAGGGGCAAAGAATAAGAGCACAGAAGAAGAGAAAAGACGAAG

AGCAGAAGCGGAAAACGTATA-3'

ERG9p-OLIGO-F
                                          (SEQ ID NO: 30)
CTAGAGACCCTGCGAGCGTGTC

ERG9p-OLIGO-R
                                          (SEQ ID NO: 31)
TATACGTTTTCCGCTTCTGCTCTTC
```

(5) Modification and Transformation of Cas 9 Vector

Because screening marker TRP of p414-TEF1p-Cas9-CYC1t vector (from Addgene co.) is not suitable for BY4741 yeast, TRP screening marker was replaced by LEU, by seamless splicing in this experiment, in which LEU sequence template is eukaryotic expression vector pESC-LEU (from Agilent Technologies, Co.) was used in this experiment.

Cas9 Vector Modification Primers

| Vector | Sequence (5'-3') | SEQ ID No. |
|---|---|---|
| U-F | ATAGCTTGTCACCTTACGTACAATCTTGATCCGGAGCT | 32 |
| U-R | CTTAGGGGCAGACATACTCCAAGCTGCCTTTGTGT | 33 |
| LEU-F | AAGGCAGCTTGGAGTATGTCTGCCCCTAAGAAGAT | 34 |
| LEU-R | TACTACTCAGTAATAACTTAAGCAAGGATTTTCTTAACTTC | 35 |
| D-F | AGAAAATCCTTGCTTAAGTTATTACTGAGTAGTATTTAT | 36 |
| D-R | AGGGTGATGGTTCACGTAGTGGGCCATCGCCCTGA | 37 |

(i) using pESC-LEU plasmid as template to amplify LEU sequence, p414-TEF1p-Cas9-CYC1t plasmid as template to amplify upstream sequence and downstream sequence of TRP, in which primers are LEU-F/R, U-F/R and D-F/R, respectively.

| system: | NEB Phusion Master Mix | 25 μL |
|---|---|---|
| | Primer1 | 2.5 μL |
| | Primer2 | 2.5 μL |
| | template | 1.5 μL |
| | ddH2O | up to 50 μL |
| condition: | 98° C. 30 s | |
| | 98° C. 10 s | |
| | 62° C. 15 s | 35 cycles |
| | 72° C. 2~4 kb/min | |
| | 72° C. 5 min | |
| | 4° C. hold | |

(ii) Double digestion of p414-TEF1p-Cas9-CYC1t plasmid SnaBI restriction endonuclease site of upstream 148 bp of TRP1 ORF and DraIII restriction endonuclease site of downstream 323b were selected.

| system: | Cutsmart buffer | 5 μL |
|---|---|---|
| | SnaBI-HF | 1 μL |
| | DraIII-HF | 1 μL |
| | p414-TEF1p-Cas9-CYC1t | 2 μg |
| | ddH2O | up to 50 μL |
| conditions: | 37° C. 2 h | |

(iii) Glue cutting to recover each fragment (iv) In-Fusion reaction

| system: | 5 × In-Fusion HD Enzyme Premix | 2 μL |
|---|---|---|
| | Linearized Vector | 0.01~0.25 pmol |
| | Insert | 0.01~0.25 pmol |
| | ddH2O | up to 10 μL |

Note: n(vector):n(fragment)=1:2 conditions: incubated at 50° C. for 15 min; and placed on ice.

(v) transforming 10 μL of splicing products into 50 μL Trans1-T1 competent cells, resuscitated at 30° C., coated with LB+Amp solid medium (from Beijing FunGenome Technology Co., Ltd.), and cultured overnight at 30° C.

(vi) selecting single colony, which was cultured in shake flask with LB+Amp liquid medium at 30° C., 250 rpm for 4 to 6 hours, bacterial liquid is subjected to PCR verification, primers as follows: if the PCR product was detected by agarose gel electrophoresis that there is a band around 1740 bp, corresponding bacterial liquid would be sent to the company for sequencing.

Modification of PCR Primers in Bacterial Liquid with Cas9 Vector

| Primer | Sequence (5'-3') | SEQ ID No. |
|---|---|---|
| ScCas9-F | GCACCATAAACGACATTACTATA | 38 |
| ScCas9-R | ACCCCAAAAAACTTGATTAGG | 39 |

(vii) bacteria liquid with correct sequencing was cultured in shake flask, modified cas9 plasmid (Leu2-TEF1p-Cas9-CYC1t) was extracted.

(viii) transforming the modified Cas9 plasmid into BY4741 yeast strain, transformation method of which was according to specification of Frozen-EZ Yeast Transformation II™ (from Zymo Research co.) to obtain strain BY4741-Cas9.

(6) transforming gRNA and dsOligo into BY4741-Cas9
taking about 500 ng of gRNA, 2 μg of erg9p dsOligo, 1 μg of rox1 dsOligo, according to different knockout purposes, mixed system was added to 100 μL of BY4741-Cas9 competent cells, and electrotransformation was performed.

(7) Acquisition of Mutant Strains
modified strain in step (6) was detected with a pair of screened primers, using unmodified strain as control. primer sequence is as follows:

```
rox1-D-F
                                    (SEQ ID NO: 40)
TCCTCGTATTGTCTTGCCGG rox1-D-R
                                    (SEQ ID NO: 41)
CTAGACCACCTGCGCCTAAC erg9p-D-F
                                    (SEQ ID NO: 42)
CTAGAGACCCTGCGAGCGTG erg9p-D-R
                                    (SEQ ID NO: 43)
CAGCTACGTAGTGACAGTAC
```

After PCR screening, positive clones were sequenced and identified, and mutated strains were obtained.

(8) removal of Cas9 and gRNA plasmids (i) putting BY4741 mutant strain into YPD solid medium (from Beijing FunGenome Technology Co., Ltd.) and culturing at 42° C. for 3 days to grow a single colony;

(ii) selecting single colony, culturing in shake flask at 42° C. in liquid medium with same composition, and subculturing twice;

(iii) BY4741 mutant strains cultured in (ii) were put into YPD, SC-LEU and SC-URA solid medium (from Beijing FunGenome Technology Co., Ltd.) and cultured at 30° C. for 3 days. If BY4741 modified strain could grow normally on YPD solid medium but could not grow on both of SC-LEU and SC-URA solid medium, it was proved that both of Cas9 and gRNA plasmids had been removed;

(iv) culturing the mutant strain without plasmid in liquid medium with shake flask, then sequencing the same again according to the method in (7) to ensure that the mutation was correct to get two kinds of mutant strains BY4741 erg9::Δ-200-176 and BY4741 erg9::Δ-200--176 rox1::mut.

Embodiment 5: Construction of Engineered Bacteria for Producing Cryptomeridiol

The plasmid pYX212-TwCS in embodiment 3 is transformed into strain BY4741, in which transformation method thereof is according to specification of Frozen-EZ Yeast Transformation II™ (from Zymo Research Co.), and engineered bacteria TE1 is obtained, as shown in Table 1 and FIG. 1.

The plasmid pYX212-ERG20+TwCS in embodiment 3 is transformed into strain BY4741, in which transformation method thereof is according to specification of Frozen-EZ Yeast Transformation II™ (from Zymo Research Co.), and engineered bacteria TE2 is obtained, as shown in Table 1 and FIG. 1.

The plasmid pYX212-IDI+TwCS in embodiment 3 is transformed into strain BY4741, in which transformation method thereof is according to specification of Frozen-EZ Yeast Transformation II™ (from Zymo Research Co.), and engineered bacteria TE3 is obtained, as shown in Table 1 and FIG. 1.

The plasmid pYX212-(IDI-ERG20)+TwCS in embodiment 3 is transformed into strain BY4741, in which transformation method thereof is according to specification of Frozen-EZ Yeast Transformation II™ (from Zymo Research Co.), and engineered bacteria TE4 is obtained, as shown in Table 1 and FIG. 1.

The plasmid pYX212-(EGR20-IDI)+TwCS in embodiment 3 is transformed into strain BY4741, in which transformation method thereof is according to specification of Frozen-EZ Yeast Transformation II™ (from Zymo Research Co.), and engineered bacteria TE5 is obtained, as shown in Table 1 and FIG. 1.

The plasmids pYX212-(ERG20-IDI)+TwCS and p424-tHMG1 in embodiment 3 are transformed into strain BY4741, in which transformation method thereof is according to specification of Frozen-EZ Yeast Transformation II™ (from Zymo Research Co.), and engineered bacteria TE6 is obtained, as shown in Table 1 and FIG. 1.

The plasmids pYX212-IDI+TwCS and p424-tHMG1 in embodiment 3 are transformed into strain BY4741, in which transformation method thereof is according to specification of Frozen-EZ Yeast Transformation II™ (from Zymo Research Co.), and engineered bacteria TE7 is obtained, as shown in Table 1 and FIG. 1.

The plasmids pYX212-IDI+TwCS and p424-tHMG1 in embodiment 3 are transformed into mutant strain BY4741 erg9::Δ-200-176, in which transformation method thereof is according to specification of Frozen-EZ Yeast Transformation II™ (from Zymo Research Co.), and engineered bacteria TE8 is obtained, as shown in Table 1.

The plasmids pYX212-IDI+TwCS and p424-tHMG1 in embodiment 3 are transformed into mutant strain BY4741 erg9::Δ-200-176 rox1::mut, in which transformation method thereof is according to specification of Frozen-EZ Yeast Transformation II™ (from Zymo Research Co.), and engineered bacteria TE2 is obtained, as shown in Table 1.

TABLE 1 genotypes and recombinant plasmids of the strains involved in embodiment of the invention

| strain | Genotypes and foreign plasmids | Origin |
|---|---|---|
| BY4741 | MATa; his3Δ1; leu2Δ0; met15Δ0; ura3Δ0 | ATCC |
| TE1 | BY4741/pYX212-TwCS | embodiment |

TABLE 1-continued genotypes and recombinant plasmids of the strains involved in embodiment of the invention

| strain | Genotypes and foreign plasmids | Origin |
|---|---|---|
| TE2 | BY4741/pYX212-ERG20 + TwCS | embodiment |
| TE3 | BY4741/pYX212-IDI + TwCS | embodiment |
| TE4 | BY4741/pYX212-(IDI-ERG20) + TwCS | embodiment |
| TE5 | BY4741/pYX212-(ERG20-IDI) + TwCS | embodiment |
| TE6 | BY4741/pYX212-(ERG20-IDI) + TwCS/p424-tHMG1 | embodiment |
| TE7 | BY4741/pYX212-IDI + TwCS/p424-tHMG1 | embodiment |
| TE8 | BY4741 erg9::Δ-200--176/pYX212-IDI + TwCS/p424-tHMG1 | embodiment |
| TE9 | BY4741 erg9::Δ-200--176 rox1::mut/pYX212-IDI + TwCS/p424-tHMG1 | embodiment |

Embodiment 6: Engineered Bacteria Cultivation and Product Identification (1) Engineered Bacteria Cultivation Strain was fermented to produce sesquiterpene by a bioreactor. 20 g/L of glucose was used as carbon source, and corresponding dropout medium (from Beijing FunGenome Technology Ltd) was used to pre-culture corresponding nutrient dropout strains. Medium for 3 L bioreactor was composed of 8 g/L of synthetic denitrification medium without uracil and histidine, 10 g/L $(NH_4)_2SO_4$, 10 g/L of $KH_2PO_4$, 1.0 g/L of $MgSO_4 \cdot 7H_2O$. 50% $NH_3H_2O$ used as pH regulator. The strain was pre-cultured in a shake flask at a speed of 230 rpm and at 30° C. for 48 h. Then in the 3 L stirred-tank bioreactor (Eppendorf BioFlo/CelliGen 115), 1 L of fermentation medium was inoculated with the pre-culture cells. 500 g/L glucose solution was periodically to maintain growth of the strains. A concentrated medium with 40 g/L synthetic denitrification medium lacking uracil and histidine and 100 g/L $(NH_4)_2SO_4$ was fermented.

(2) Extraction and Separation of Products

Fermentation products are sesquiterpene component, which are easily soluble in n-hexane, which is thus selected as the extraction reagent. Fermentation broth was centrifuged into two parts of cell and bacterial liquid, and same volume of n-hexane was added to the bacterial liquid then extracted for 3 times; after the cell was broken, ultrasonic extraction was performed for three times, with 3 times of volume of n-hexane. Organic layer was combined, an appropriate amount of anhydrous sodium sulfate was added, with resting for a while to remove water from the extraction liquid. The extraction liquid is concentrated extract with a rotary evaporator, in which temperature for water bath should not exceeding 35° C. (volatile components), and finally produce is transferred to a glass collection bottle.

Taking a silica gel thin plate, concentrated products were expanded with n-hexane and ethyl acetate in different ratios, with vanillin sulfuric acid as chromogenic agent. Preliminary separation: then separating the same by XSelect CSH Prep C18 OBD (19×150 mm, 5 um) column, mobile phase A was 0.1% (v/w) formic acid water, and mobile phase B was acetonitrile, with flow rate of 20 mL/min. Concentration and enrichment of monomer compounds are separated.

(3) Structural Identification

Figure 2:
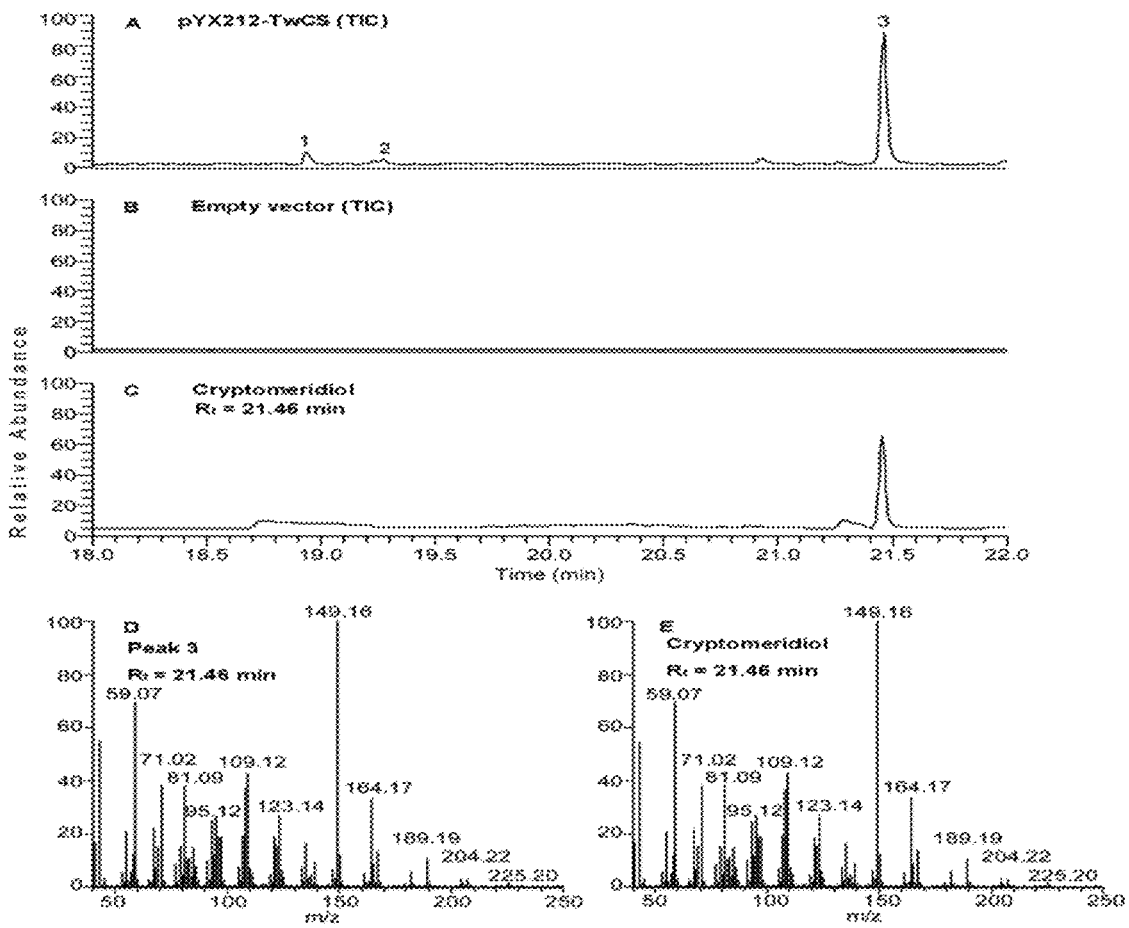
FIG. 2 is a fermentation product diagram of GC-MS analysis, in which A is fermentation product of strain TE1, product with peak position at 1 and 2 is small amount of sesquiterpene (peak position 1 is eucalyptol), and the product with peak position at 3 is identified as cryptomeridiol with retention time of 21.43 min; B is a product diagram which is expressed in empty vector without TwCS expression gene, in which there is no sesquiterpene product found; C is a GC-MS diagram of a standard product of cryptomeridiol with peak position being same as that of the peak 3 in FIG. 1; D and E are mass spectrums of product of the peak position 3 of TE1 and the standard product of cryptomeridiol, respectively.

The structure of the compound was analyzed by NMR spectrum. All data were collected from BRUKER ACANCE III 600 MHz spectrometer. Solvent was deuterated chloroform containing TMS. The compound was finally identified as cryptomeridiol, as shown in FIG. 2.

Figure 3:
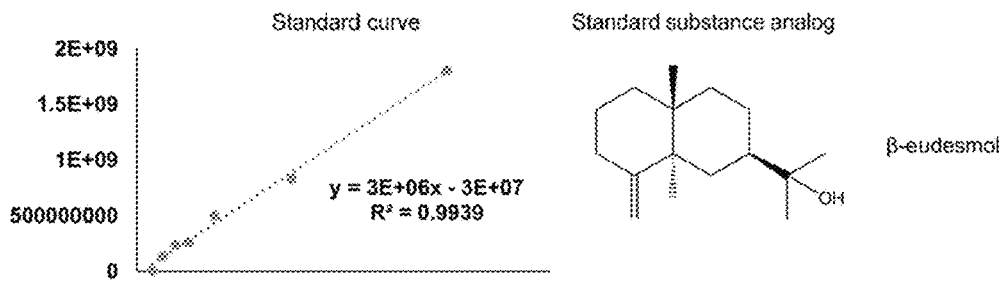
FIG. 3 is a standard curve diagram for quantification of the standard product of cryptomeridiol.
Figure 4:
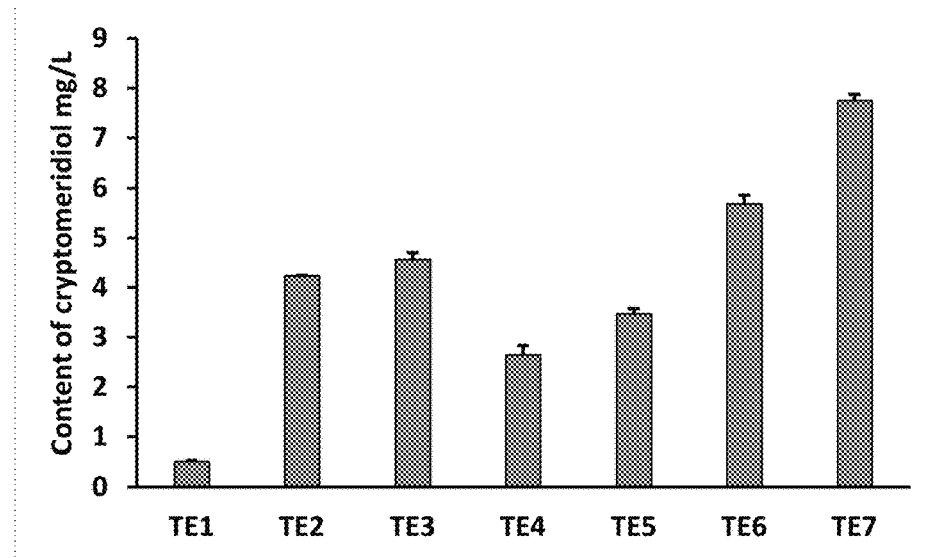
FIG. 4 is a yield determination diagram of cryptomeridiol product expressed by TE1-TE7 strains.
Figure 5:
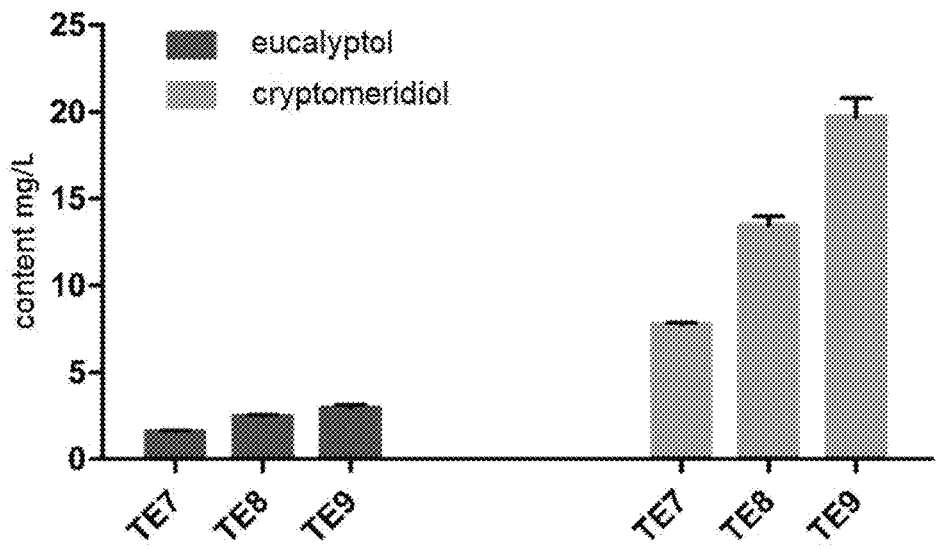
FIG. 5 is a comparative diagram of expression yields of cryptomeridiol and eucalyptol between mutant strains TE8 and TE9 obtained by CRISP/Cas9 gene editing.

Embodiment 7: Comparison of Yields of Cryptomeridiol Produced by Engineered Bacteria In order to determine the sesquiterpene production of each strain, inoculation is at ratio of 1:100, and 50 mL solution was pre-cultured as the strain. The strain was cultured in defective medium containing 20 g/L glucose at 230 rpm at 30° C. After shaking culture for 72 hours, OD600 of all strains was detected. Same volume of n-hexane was added to culture liquid, then keeping oscillating under 200 rpm for 2 hours, and adding same volume of n-hexane for ultrasonic extraction twice. Organic layer is merged, evaporated in rotation and concentrated. Finally, the concentrated sample was fixed to 1.0 mL, then 100 uL thereof was taken to prepare GC-MS sample for GC-MS analysis. Using Thermo TRACE 1310/TSQ8000 gas chromatograph (no shunt; syringe temperature at 250 m ° C.), TG-5 MS (30 m×0.25 mm×0.25 m) capillary column; GC conditions are as follows: first, keeping the oven temperature constant at 50° C. for 2 minutes, then rising to 280° C. at speed of 8° C./min and keeping at the final temperature for 10 minutes. Temperature of syringe and detector is 50° C. Standard curve was established by using P-eudesmol as analogue of cryptomeridiol, and the standard curve equation was obtained as $y=3E+06x-3E+07$, as shown in FIG. 3.

The specific output is calculated as follows:

| TE1 | 0.516 mg/L |
|---|---|
| TE2 | 4.24 mg/L |
| TE3 | 4.57 mg/L |
| TE4 | 2.65 mg/L |
| TE5 | 3.47 mg/L |
| TE6 | 5.68 mg/L |
| TE7 | 7.75 mg/L |
| TE8 | 13.47 mg/L |
| TE9 | 19.73 mg/L |

Above description is not a limitation to the present invention, nor is the invention limited to the above examples. Any changes, modifications, additions or replacements made by ordinary technical personnel in the technical field within the substantive scope of the invention shall also fall within the protection scope of the invention, and the protection scope of the invention shall be subject to the claims.

The invention claimed is:

1. A yeast engineered bacteria with high yield of cryptomeridiol, wherein the yeast engineered bacteria comprises a gene coding a cryptomeridiol synthase with amino acid sequence as SEQ ID NO:2, and at least one of erg9 and rox1 genes is knocked out from the yeast engineered bacteria.

2. The yeast engineered bacteria as in claim 1, wherein the gene coding a cryptomeridiol synthase with amino acid sequence as SEQ ID NO:2 is at least one of:

(1) nucleotide molecule shown in SEQ ID NO:1;
(2) nucleotide sequence resulted from the nucleotide molecule shown in SEQ ID NO:1 being substituted, deleted or added with one or more nucleotide, with expressing same function of protein;
(3) nucleotide sequence hybridized with the nucleotide molecules shown in SEQ ID NO:1 under stringent conditions, wherein the stringent conditions are that hybridizing in 0.1×SSPE solution containing 0.1% of SDS or in 0.1×SSC solution containing 0.1% of SDS.

3. The yeast engineered bacteria as in claim 1, wherein erg9 gene is knocked out from the yeast engineered bacteria, or erg9 and rox1 genes are knocked out from the yeast engineered bacteria.

4. The yeast engineered bacteria as in claim 1, which contains following gene fragments resulting from homologous recombination on the yeast self and integration into genome thereof:
- recombinant expression vector pYX212-IDI+TwCS, which is constructed from promoter TPIp, IDI gene, yeast terminator FBA1t, yeast promoter TEF1p, cryptomeridiol synthase expression gene TwCS, and terminator pYX12t into plasmid pYX212;
- recombinant expression vector p424-tHMG1, which is constructed from yeast promoter TDH3p, gene tHMG1 of truncated HMG-COA reductase with amino acid sequence as SEQ ID NO:44, and yeast terminator TDH3t into plasmid p424, wherein gene tHMG1 encodes amino acid as SEQ ID NO:44.

5. The yeast engineered bacteria as in claim 1, wherein the yeast engineered bacteria is GEN.PK series of *Saccharomyces cerevisiae* or BY series of *Saccharomyces cerevisiae*.

6. The yeast engineered bacteria as in claim 5, wherein the BY series of *Saccharomyces cerevisiae* is BY4741 *Saccharomyces cerevisiae*.

7. A method for building the engineered bacteria as in claim 1, comprising steps of:

(1) constructing mutant strains:
- knocking out the erg9 gene in the BY4741 yeast strain, to obtain mutant strain BY4741erg9::Δ-200--176; or
- knocking out the erg9 gene and the rox1 gene in the BY4741 yeast strain, to obtain mutant strain BY4741 erg9::Δ-200--176 rox1::mut;

(2) constructing recombinant expression vectors pYX212-IDI+TwCS and p424-tHMG1;

(3) transforming recombinant expression vectors pYX212-IDI+TwCS and p424-tHMG1 into the mutant strain BY4741 erg9::Δ-200--176, to obtain yeast engineering strain TE8; or
- transforming recombinant expression vectors pYX212-IDI+TwCS and p424-tHMG1 into the mutant yeast strain BY4741 erg9::Δ-200--176 rox1::mut to obtain the yeast engineering strain TE9.

8. The method of claim 7, wherein a method for constructing the mutant strain is a modification by CRISP/Cas9 gene editing technology.

9. The method of claim 8, wherein in the CRISP/Cas9 gene editing technology, an expression vector containing Cas9 is a p414-TEF 1p-Cas9-CYC1t vector, and TRP screening marker in the p414-TEF1p-Cas9-CYC1t vector is replaced with LEU screening marker.

10. A method of synthesis of cryptomeridiol or eucalyptol using the engineered bacteria of claim 1.

\* \* \* \* \*